(12) United States Patent
Yagyu et al.

(10) Patent No.: US 11,331,265 B2
(45) Date of Patent: *May 17, 2022

(54) ULTRAVIOLET BLOCKING AGENT AND COSMETIC PRODUCT

(71) Applicant: SHODOSHIMA HEALTHYLAND CO., LTD., Kagawa (JP)

(72) Inventors: Toshihiro Yagyu, Shozu-gun (JP); Norihito Kishimoto, Shozu-gun (JP); Kana Iwata, Shozu-gun (JP)

(73) Assignee: SHODOSHIMA HEALTHYLAND CO., LTD., Kagawa (JP)

( * ) Notice: Subject to any disclaimer, the term of this patent is extended or adjusted under 35 U.S.C. 154(b) by 139 days.

This patent is subject to a terminal disclaimer.

(21) Appl. No.: 16/944,614

(22) Filed: Jul. 31, 2020

(65) Prior Publication Data

US 2020/0405623 A1 Dec. 31, 2020

Related U.S. Application Data

(62) Division of application No. 15/745,949, filed as application No. PCT/JP2016/084502 on Dec. 1, 2016, now abandoned.

(30) Foreign Application Priority Data

Dec. 1, 2015 (JP) ................................ 2015-234470

(51) Int. Cl.
| | | |
|---|---|---|
| *A23L 33/105* | (2016.01) | |
| *A61Q 17/04* | (2006.01) | |
| *A61K 8/9789* | (2017.01) | |
| *A61K 36/63* | (2006.01) | |
| *A23L 33/10* | (2016.01) | |
| *A61K 8/60* | (2006.01) | |

(52) U.S. Cl.
CPC ............ *A61K 8/9789* (2017.08); *A23L 33/10* (2016.08); *A23L 33/105* (2016.08); *A61K 8/602* (2013.01); *A61K 36/63* (2013.01); *A61Q 17/04* (2013.01); *A23V 2002/00* (2013.01)

(58) Field of Classification Search
None
See application file for complete search history.

(56) References Cited

U.S. PATENT DOCUMENTS

| 6,146,637 A | 11/2000 | Amari |
| 10,258,660 B2 * | 4/2019 | Yagyu ..................... A61P 29/00 |
| 2002/0054927 A1 | 5/2002 | Paufique |
| 2002/0110600 A1* | 8/2002 | Voorhees ............... A61K 36/63 |
| | | 424/769 |
| 2003/0108651 A1 | 6/2003 | Crea |
| 2003/0152656 A1 | 8/2003 | Pinnell et al. |
| 2008/0014322 A1* | 1/2008 | Ibarra ................... A23L 33/105 |
| | | 426/330.6 |
| 2013/0196937 A1* | 8/2013 | Shimoda ................. A61P 13/12 |
| | | 514/27 |
| 2013/0243709 A1 | 9/2013 | Hanson et al. |

FOREIGN PATENT DOCUMENTS

| EP | 2 338 500 A1 | 6/2011 |
| JP | 2000-128765 A | 5/2000 |
| JP | 2001-122758 A | 5/2001 |
| JP | 2001-336064 A | 12/2001 |
| JP | 2002-332238 A | 11/2002 |
| JP | 2003-246724 A | 9/2003 |
| JP | 2010-067050 A | 3/2010 |
| JP | 2011-125301 A | 6/2011 |
| JP | 2012-201850 A | 10/2012 |

OTHER PUBLICATIONS

The Olive Oil Series Kesho Shitaji the UV Protector, Bihada Mania (online), <https://web.archive.org/web/20150930003440/http://www.bihada-mania.jp/cosme/25538>, (2015).

Kojima, Hiroyuke, "Protection against UV-A with plant extracts.", Fragrance Journal, vol. 25, No. 3, pp. 56-61, (1996).

Feb. 14, 2017 International Search Report issued in Patent Application No. PCT/JP2016/084502.

P. Peru Gini et al.: "Efficacy of oleuropein against UVB irradiation preliminary evaluation", International Journal of Cosmetic Science, vol. 30, 2008, pp. 113-120.

Liakopoulos, Georgios: "Trichome layers versus dehaired lamina of Olea europa ea leaves: Differences in flavonoid distribution, UV-absorbing capacity, and wax yield", Environmental and Experimental Botany, vol. 55, 2006, pp. 294-304.

A. Issaoui et al: "Composition of the olive tree bark: Richness in oleuropein", Trends in Chemical Engineering, vol. 14, 2012, pp. 65-69.

Apr. 15, 2019 Euorpean Search Report issued in European Patent Application No. 16870486.4.

Jul. 7, 2021 Office Action issued in Australian Patent Application No. 201636061.

\* cited by examiner

*Primary Examiner* — Robert T. Crow
*Assistant Examiner* — John P Nguyen
(74) *Attorney, Agent, or Firm* — Oliff PLC

(57) ABSTRACT

The present disclosure is directed to a method for producing an olive branch extract having a high oleuropein content. The method includes crushing at least a portion of dried olive branch and extracting olive branch extract from the crushed olive branch with an extraction solvent. The olive variety is at least one selected from Lucca, Mission, and Nevadillo Blanco. The added branch amount of olive branch to the extraction solvent is 10% by weight or more, the extraction solvent is 30% to 50% 1,3-butylene glycol, and the extraction is performed at a temperature in a range of 70° C. to 80° C.

8 Claims, 5 Drawing Sheets

ULTRAVIOLET BLOCKING AGENT AND COSMETIC PRODUCT

This is a Division of application Ser. No. 15/745,949 filed Jan. 18, 2018, which in turn is a National Stage Application of PCT/JP2016/084502 filed on Nov. 21, 2016, which claims the benefit of Japanese Application No. 2015-234470 filed Dec. 1, 2015. The disclosure of the prior applications is hereby incorporated by reference herein in its entirety.

TECHNICAL FIELD

The present invention relates to an ultraviolet blocking agent and a cosmetic product.

BACKGROUND ART

Ultraviolet is electromagnetic waves of invisible light rays with wavelengths of 10 nm to 400 nm and has various chemical effects. In particular, near-ultraviolet with wavelengths of about 380 nm to 200 nm is classified into UV-A (320 nm to 400 nm), UV-B (290 nm to 320 nm), and UV-C (200 nm to 290 nm) in terms of the effects on human health and environment. UV-A and UV-B included in sunlight pass through the ozone layer to reach the earth's surface. UV-A is known to reach the dermis layer of skin to denature protein, causing the skin to lose its elasticity and accelerating aging. UV-B is known to act on the epidermis layer of skin to generate melanin in pigment cells and cause sunburn. Ultraviolet may cause diseases such as skin cancer.

In order to suppress these effects by ultraviolet, a variety of substances having the ultraviolet blocking action are disclosed. For example, Patent Document 1 describes a fiber or a fiber structure having tea polyphenols fixed thereon to absorb and suppress ultraviolet in the invisible wavelength range included in sunlight.

Olive is a plant in the family of Oleaceae, originated from the Mediterranean Coast and traditionally cultivated for eating and for obtaining oil. The olive fruit ripe around December contains about 15% to 30% of oil, and olive oil is obtained by pressing the olive fruit in this season. The thus obtained olive fruit and olive oil are known to have various excellent effects such as alleviating arteriosclerosis, gastric ulcer, and obstipation, strengthening bones, preventing aging, and skin-beautifying actions.

Olive leaves are known to have a vitamin A content much higher than the olive fruit and be rich in vitamin E as an antioxidant as well as chlorophyll and others having an anti-inflammatory action and deodorant and antibacterial actions.

The olive fruit and leaves contain polyphenols, and, for example, their health enhancing actions have also drawn attention. Oleuropein, which is a kind of polyphenols contained in olive leaves, particularly has a very high antioxidant potency, and the effect of preventing and ameliorating various diseases have been noted.

As a method of extracting an olive leaf extract, for example, Patent Document 2 discloses a method of producing an olive leaf extract including oleuropein by drying and grinding olive leaves, followed by extraction using water, water containing citric acid, or water containing peptide as an extraction solvent.

PRIOR ART DOCUMENTS

Patent Document

Patent Document 1: Japanese Patent Application Publication No. 2001-336064 (JP 2001-336064 A)

Patent Document 2: Japanese Patent Application Publication No. 2011-125301 (JP 2011-125301 A)

SUMMARY OF THE INVENTION

Problem to be Solved by the Invention

An object of the present invention is to provide a new ultraviolet blocking agent and a cosmetic product having a high ultraviolet blocking action.

Means for Solving the Problem

The inventors of the present invention have found that the extract obtained from branches of olive has a high effect of absorbing ultraviolet, in particular, UV-A and UV-B and has a high ultraviolet absorbing action. The inventors of the present invention have completed the invention based on this finding.

The present invention provides an ultraviolet blocking agent comprising an extract of branches of olive.

The present invention provides an ultraviolet blocking agent, in which a total polyphenol content per 100 g of the ultraviolet blocking agent is not less than 100 mg.

The present invention provides an ultraviolet blocking agent, in which the branches of olive are bark of olive.

The present invention provides an ultraviolet blocking agent in a form of a cosmetic product.

The present invention further provides a method of blocking ultraviolet radiation to a target, comprising applying an extract of branches of olive to skin.

Effects of the Invention

The present invention can provide an ultraviolet blocking agent and a cosmetic product having a high ultraviolet blocking action.

MODES FOR CARRYING OUT THE INVENTION

Figure 1:
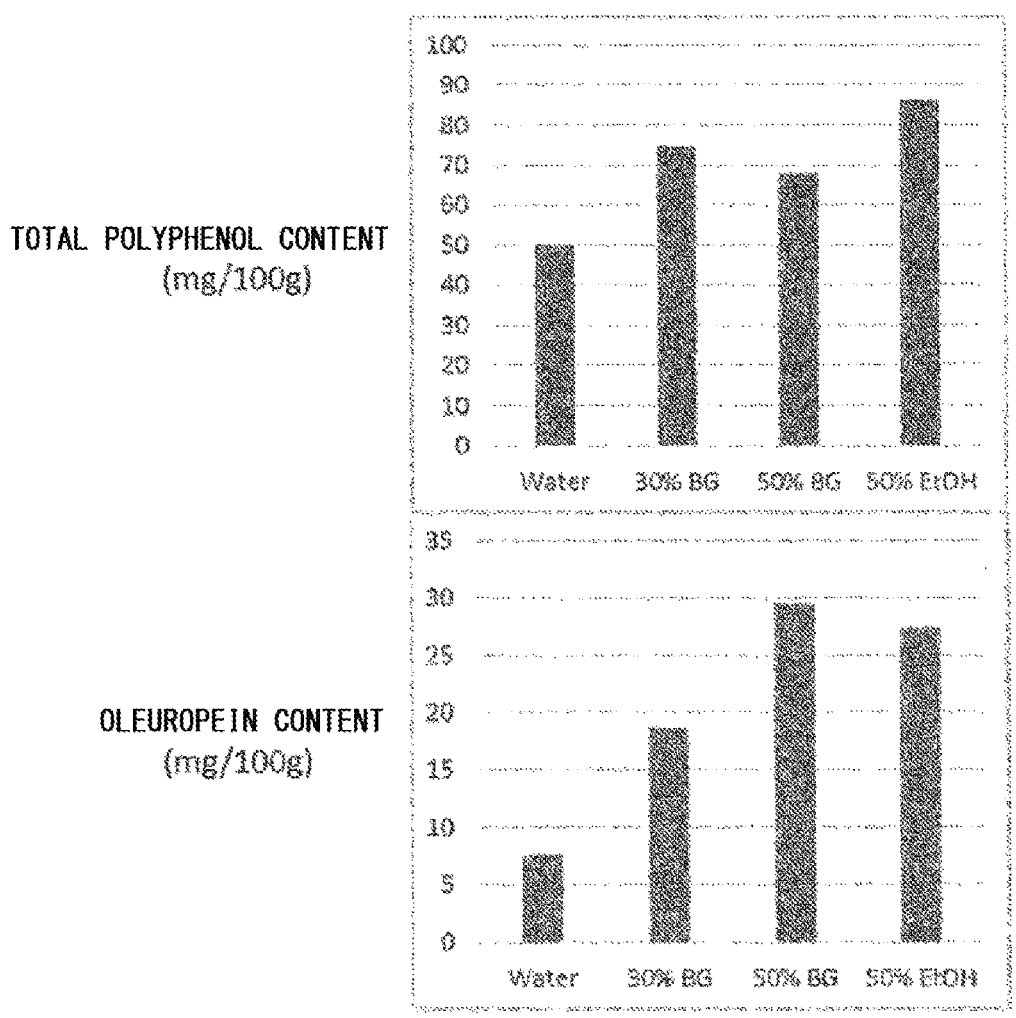
FIG. 1 is a graph illustrating the total polyphenol content (mg/100 g) and the oleuropein content (mg/100 g) of olive branch extracts extracted using a variety of extraction solvents.

The present invention provides an ultraviolet blocking agent containing an extract of branches of olive (which hereinafter may be referred to as "olive branch extract").

The olive branch extract is an extract derived from branches of olive. In the present description, "branches of olive" or "olive branches" includes branches, stems, and bark of olive trees. That is, in the present description, "olive branch extract" includes olive branch extract, olive stem extract, and olive bark extract. The extract of branches of olive contains many polyphenols such as oleuropein and hydroxytyrosol.

Examples of the cultivars of branches of olive that may be used in the present invention include Lucca, Mission, Nevadillo Blanco, Manzanillo, Amellenque, Arbequina, Ascolana Terena, Ascolano, Azapa, Barnea, Barouni, Biancolilla, Bidh El Hamman, Blanqueta, Caillet Blane, Carolea, Cayonne, Chemilali, Chitoni, Cipressino, Coratina, Cornicabra, Correggiola, Cucco, Gigante di Cerignola, Frantoio, Glappolo, Gordal, Hardy's Mammoth, Hojiblanca, Itrana, Jumbo Kalamata, Kalamata, Koroneiki, Leccino, Leccio del Corno, Liani, Lucques, Manzanilla, Maurino, Michellenque, Moraiolo, Nabali Mohassan, Nab Tamri, Negral, Nocellara del Belice, Obliza, Oblonga, Paragon, Pendolino, Picual, Redding picholine, Redounan, Saurin large leaf, Saurin medium leaf, Saurin small leaf, Sevillano, Sorani, South Australian Verdale, St. Catherin, Taggiasca, Tanche, Tiny Oil Kalamata, Tsunati, Verdale, Wagga Verdale, Zarza, Oliviẽre, and FS17. In the present invention, the cultivars of branches of olive may be used singly or in combination of two or more.

The total polyphenol content per 100 g of the ultraviolet blocking agent according to the present invention is, for example, not less than 100 mg, preferably not less than 200 mg, more preferably not less than 300 mg. The oleuropein content per 100 g of the ultraviolet blocking agent according to the present invention is not less than 30 mg, preferably not less than 50 mg, more preferably not less than 100 mg.

As illustrated in Examples described later, the olive branch extract has the effect of absorbing, in particular, UV-A and UV-B of ultraviolet. Thus, the ultraviolet blocking agent according to the present invention can effectively block UV-A and UV-B and therefore can prevent the effects by ultraviolet, such as aging of skin, sunburn, and skin cancer. The ultraviolet blocking agent according to the present invention can be used for pharmaceutical drugs, medicines, quasi-drugs, cosmetics, foods, and others having an ultraviolet blocking action and, for example, can be used for cosmetic products and skin drugs for external use having sunscreen effects.

The ultraviolet blocking agent according to the present invention can be in the form of a cosmetic product. The ultraviolet blocking agent according to the present invention can be, for example, basic skin care products such as skin toner, skin milk, cream, serum, lotion, essence, hand cream, lip balm, and facial mask; makeup cosmetic products such as lipstick, lip gloss, foundation, makeup base, liquid foundation, makeup pressed powder, blusher, face powder, eye shadow, mascara, eye liner, and eyebrow makeup; cleansing cosmetic products such as facial wash, body shampoo, shampoo, and soap; cosmetic products for hair or scalp such as hair tonic, hair cream, rinse, conditioner, and hairdressing; and bath products.

The ultraviolet blocking agent according to the present invention can be in any of liquid, solid, emulsion, cream, gel, and paste forms.

The ultraviolet blocking agent according to the present invention may contain the olive branch extract alone or may further contain another ingredient. Examples of another ingredient include oily ingredients, surfactants (synthetic and natural), moisturizers, thickeners, preservatives, germicides, powder ingredients, ultraviolet absorbers, antioxidants, pigments, and fragrance. Other physiologically active ingredients may be further contained as long as the effects of the ultraviolet blocking agent according to the present invention can be retained.

Here, the oily ingredients that can be used include, for example, plant-derived oils and fats such as olive oil, jojoba oil, castor oil, soybean oil, rice oil, rice germ oil, coconut oil, palm oil, cacao oil, meadowfoam oil, shea butter, tea tree oil, avocado oil, macadamia nut oil, and plant-derived squalane; animal-derived oils and fats such as mink oil and turtle oil; waxes such as beeswax, carnauba wax, rice wax, and lanolin; hydrocarbons such as liquid paraffin, Vaseline, paraffin wax, and squalane; fatty acids such as myristic acid, palmitic acid, stearic acid, oleic acid, isostearic acid, and cis-11-eicosenoic acid; higher alcohols such as lauryl alcohol, cetanol, and stearyl alcohol; synthetic esters and synthetic triglycerides such as isopropyl myristate, isopropyl palmitate, butyl oleate, 2-ethylhexyl glyceride, and higher fatty acid octyldodecyl (such as octyldodecyl stearate).

The surfactants that can be used include, for example, nonionic surfactants such as polyoxyethylene alkyl ethers, polyoxyethylene fatty esters, polyoxyethylene sorbitan fatty esters, glycerol fatty esters, polyglycerol fatty esters, polyoxyethylene glycerol fatty esters, polyoxyethylene hydrogenated castor oils, and polyoxyethylene sorbitol fatty esters; anionic surfactants such as fatty acid salts, alkyl sulfates, alkyl benzene sulfonates, polyoxyethylene alkyl ether sulfates, polyoxyethylene fatty amine sulfates, polyoxyethylene alkyl phenyl ether sulfates, polyoxyethylene alkyl ether phosphates, α-sulfonated fatty acid alkyl ester salts, and polyoxyethylene alkyl phenyl ether phosphates; cationic surfactants such as quaternary ammonium salts, primary to tertiary fatty amine salts, trialkylbenzylammonium salts, alkyl pyridinium salts, 2-alkyl-1-alkyl-1-hydroxy ethyl imidazolinium salts, N,N-dialkylmorpholinium salts, and polyethylene polyamine fatty acid amide salts; and amphoteric surfactants such as N,N-dimethyl-N-alkyl-N-carboxymethyl ammoniobetaines, N,N,N-trialkyl-N-alkylene ammoniocarboxybetaines, and N-acylamidopropyl-N',N'-dimethyl-N'-β-hydroxypropyl ammoniosulfobetaines.

Furthermore, as an emulsifier or an emulsifier assistant, for example, *Stevia* derivatives such as enzymatically modified *Stevia*, lecithin and derivatives thereof, lacto-fermented rice, lacto-fermented germinated rice, lacto-fermented grain (for example, wheat, beans, and cereals), and *Rhamnaceae zizyphus joazeiro* extract may be blended.

The moisturizers that can be used include, for example, glycerol, propylene glycol, dipropylene glycol, 1,3-butylene glycol, polyethylene glycols, sorbitols, xylitol, and sodium pyrrolidone carboxylate. Other examples include saccharides such as trehalose, lacto-fermented rice, mucopolysaccharides (for example, hyaluronic acid and derivatives thereof, chondroitin and derivatives thereof, and heparin and derivatives thereof), elastin and derivatives thereof, collagen and derivatives thereof, NMF-related substances, lactic acid, urea, higher fatty acid octyldodecyl, seaweed extracts, urn orchid extract, seafood-derived collagen and derivatives thereof, and a variety of amino acids and derivatives thereof.

The thickeners that can be used include, for example, brown algae, green algae, or red algae-derived ingredients such as alginic acid, agar, carrageenan, and fucoidan; polysaccharides such as urn orchid extract, pectin, locust bean gum, and aloe polysaccharides; gums such as xanthan gum, tragacanth gum, and guar gum; cellulose derivatives such as carboxymethyl cellulose and hydroxyethyl cellulose; synthetic polymers such as polyvinyl alcohols, polyvinyl pyrrolidones, carboxyvinyl polymers, and acrylate/methacrylate copolymers; hyaluronic acid and derivatives thereof, and polyglutamic acids and derivatives thereof.

The preservatives and the germicides that can be used include, for example, urea; p-oxybenzoates such as methyl p-oxybenzoate, ethyl p-oxybenzoate, propyl p-oxybenzoate, and butyl p-oxybenzoate; phenoxyethanol, dichlorophen, hexachlorophene, chlorhexidine hydrochloride, benzalkonium chloride, salicylic acid, ethanol, undecylenic acid, phenols, Germall (imidazolidinyl urea), 1,2-pentanediol, various essential oils, and birch tar.

The powder ingredients that can be used include, for example, sericite, titanium oxide, talc, kaoline, bentonite, zinc oxide, magnesium carbonate, magnesium oxide, zirconium oxide, barium sulfate, silicic acid anhydride, mica, nylon powder, polyethylene powder, silk powder, cellulose powder, grain (for example, rice, wheat, corn, and proso millet) powder, and bean (for example, soybean and Adzuki bean) powder.

The ultraviolet absorbers that can be used include, for example, ethyl p-aminobenzoate, ethylhexyl p-dimethyl aminobenzoate, amyl salicylate and derivatives thereof, 2-ethylhexyl p-methoxycinnamate, octyl cinnamate, oxybenzone, 2,4-dihydroxybenzophenone, 2-hydroxy-4-methoxybenzophenone-5-sulfonate, 4-tertiarybutyl-4-methoxybenzoylmethane, 2-(2-hydroxy-5-methylphenyl) benzotriazole, urocanic acid, ethyl urocanate, and aloe extract.

The antioxidants that can be used include, for example, butyl hydroxyanisole, butyl hydroxytoluene, propyl gallate, vitamin E and derivatives thereof, urn orchid extract, and Asian rice extract.

The physiologically active ingredients that can be used include, for example, as whitening ingredients, t-cycloamino acid derivatives, kojic acid and derivatives thereof, ascorbic acid and derivatives thereof, hydroquinone derivatives, ellagic acid and derivatives thereof, resorcinol derivatives, mulberry bark extract, *Saxifraga stolonifera* extract, rice bran extract, rice bran extract hydrolysate, lacto-fermented rice, lacto-fermented germinated rice, lacto-fermented grain (wheat, beans, cereals), white mustard hydrolysis extract, *Callicarpa japonica* extract, *Pandanus amaryllifolius* Roxb. extract, *Arcangelicia flava* Merrilli extract, chamomile extract (tradename; CHAMOMILLA ET), extract of seaweed such as *Laminaria*, extract of seagrass such as Zosteraceae, linoleic acid and derivatives or processed products thereof (for example, liposomal linoleic acid), and 2,5-dihydroxybenzoic acid derivatives. Other examples include, as skin aging-preventing and skin-beautifying ingredients, animal or fish-derived collagen and derivatives thereof, elastin and derivatives thereof, nicotinic acid and derivatives thereof, glycyrrhizic acid and derivatives thereof (for example, dipotassium salt), t-cycloamino acid derivatives, vitamin A and derivatives thereof, vitamin E and derivatives thereof, allantoin, α-hydroxy acids, diisopropylamine dichloroacetate, γ-amino-β-hydroxybutyric acid, crude drug extracts such as *Gentiana lutea* extract, *Glycyrrhiza* extract, Job's tears extract, chamomile extract, Kudzu root extract, Shiso extract, carrot extract, and aloe extract, rice extract hydrolysate, rice bran extract hydrolysate, rice ferment extract, *Chlorella* extract, brown algae extract, *Laminaria angustata* extract, *Ulva pertusa* extract, extract of seagrass such as *Zostera marina*, mulberry bark extract, and *Rhamnaceae zizyphus joazeiro* extract.

Examples of the kojic acid derivatives include kojic acid esters such as kojic acid monobutylate, kojic acid monocaprate, kojic acid monopalmitate and kojic acid dibutylate, kojic acid ethers, and kojic acid saccharide derivatives such as kojic acid glucoside. Examples of the ascorbic acid derivatives include ascorbic acid ester salts such as sodium L-ascorbic acid-2-phosphate, magnesium L-ascorbic acid-2-phosphate, sodium L-ascorbic acid-2-sulfate, and magnesium L-ascorbic acid-2-sulfate, ascorbic acid saccharide derivatives such as L-ascorbic acid-2-glucoside (2-0-α-D-glucopyranosyl-L-ascorbic acid) and L-ascorbic acid-5-glucoside (5-0-α-D-glucopyranosyl-L-ascorbic acid), the 6-position acylated products (acyl group is, for example, hexanoyl group, octanoyl group, or decanoyl group) of these ascorbic acid saccharide derivatives, L-ascorbic acid tetra fatty acid esters such as L-ascorbyl tetraisopalmitate and L-ascorbyl tetralaurate, 3-0-ethyl ascorbic acid, and sodium L-ascorbyl-2-phosphate-6-0-palmitate. Examples of the hydroquinone derivatives include arbutin (hydroquinone-β-D-glucopyranoside) and α-arbutin (hydroquinone-α-D-glucopyranoside). Examples of the resorcinol derivatives include 4-n-butylresorcinol and 4-isoamylresorcinol. Examples of the 2,5-dihydroxybenzoic acid derivatives include 2,5-diacethoxybenzoic acid, 2-acethoxy-5-hydroxybenzoic acid, and 2-hydroxy-5-propionyloxybenzoic acid. Examples of the nicotinic acid derivatives include nicotinamide and benzyl nicotinate. Examples of the vitamin E derivatives include vitamin E nicotinate and vitamin E linoleate. Examples of the α-hydroxy acid include lactic acid, malic acid, succinic acid, citric acid, and α-hydroxyoctanoic acid.

(Extraction Method of Olive Branch Extract)

The olive branch extract can be an extract derived from branches of olive by any method. The olive branch extract may be extracted, for example, from branches of olive using an extraction solvent. The extraction solvent may be, for example, water and/or alcohol.

An embodiment of the method of extracting an olive branch extract for use in the ultraviolet blocking agent according to the present invention will be described below.

The extract of branches of olive can be produced by, for example, a production method comprising a first step of grinding dried olive branches and a second step of extracting an olive branch extract from the ground olive branches using an extraction solvent.

The first step is a step of grinding dried olive branches. In the present description, "grinding" refers to physically crushing an object to reduce the size of the object, for example, physically crushing an object into fine particles, small pieces, powder, or the like. The method of drying olive branches and the method of grinding olive branches are not limited to particular methods, and any method can be used.

The picking seasons for olive branches are preferably, for example, but not limited to, the times around December when the olive fruit contains a high oil content in regions such as Japan in the Northern Hemisphere, or preferably the times after the olive fruit is fully ripe and harvested.

The second step is a step of extracting an olive branch extract from the ground olive branches using an extraction solvent. The extraction solvent includes water and/or alcohol. The alcohol includes, for example, methanol, ethanol, isopropyl alcohol, butanol, glycerol, ethylene glycol, propylene glycol, 1,3-butylene glycol, and polyethylene glycols. The extraction solvent may be water, may be 100% of alcohol, or may be alcohol diluted with water. The extraction solvent may contain 10% to 50% of alcohol. The extraction solvent may contain one alcohol alone or may include two or more alcohols. The extraction solvent may contain ingredients other than water and alcohol and may be, for example, alcohol beverages such as sake and shochu (distilled spirit).

The extraction solvent may be, for example, water, ethanol or 1,3-butylene glycol, or a combination thereof.

In the second step, the extraction temperature may be 70° C. or higher. Extraction at 70° C. or higher can yield an olive branch extract having a high polyphenol content and a high ultraviolet absorption capacity, as illustrated in Examples later. The extraction temperature may be preferably 80° C. or higher, more preferably 90° C. or higher. The upper limit of the extraction temperature may be, for example, but not limited to, 100° C. or lower.

The amount of olive branches added with respect to the extraction solvent may be, for example, but not limited to, not less than 20% by weight, preferably not less than 30% by weight. The upper limit of the amount of branches added may be, for example, but not limited to, not more than 50% by weight. This amount of branches added can yield an olive branch extract having a high polyphenol content and a high ultraviolet absorption capacity, as illustrated in Examples later.

The extract of branches of olive in the ultraviolet blocking agent according to the present invention can be produced by the production method as described above to have an ultraviolet absorption capacity higher than conventional ones. The ultraviolet blocking agent according to the present invention therefore can be used in a variety of pharmaceutical drugs, medicines, foods, and cosmetics utilizing this ultraviolet absorption capacity.

The present invention also provides a method of blocking ultraviolet radiation to a target, including administering the ultraviolet blocking agent to the target's skin. The present invention also provides a method of suppressing adverse effects on a target caused by ultraviolet, including applying the ultraviolet blocking agent to the target's skin. The adverse effects on a target caused by ultraviolet refer to any symptom caused by ultraviolet, in particular UV-A and UV-B, such as sunburn, freckles, inflammation of skin, and skin photoaging.

The target to which the method according to the present invention is applied includes mammals such as humans, mice, rats, rabbits, cats, dogs, cows, horses, and monkeys.

In the method according to the present invention, the ultraviolet blocking agent can be any ultraviolet blocking agent as described above. In the method according to the present invention, the ultraviolet blocking agent may be provided additionally with any other ingredients. In the method according to the present invention, any other ingredients include, for example, the above-noted pharmaceutically acceptable bases, carriers, excipients, binders, disintegrants, lubricants, and colorants.

In the method according to the present invention, the ultraviolet blocking agent may be applied to a target through dermal administration such as liniments and patches. In the method according to the present invention, the ultraviolet blocking agent may be administered such that a daily intake is 0.1 mg to 2,000 mg per adult. In the method according to the present invention, the ultraviolet blocking agent may be applied, but not limited to, once to seven days a week. For example, in the method according to the present invention, the ultraviolet blocking agent may be applied daily, or five or six times a week. For example, when there is a possibility of ultraviolet radiation outdoors, the ultraviolet blocking agent in the form of dermal administration can be applied to the target's skin as appropriate.

EXAMPLES (Measurement Method)

In measuring the total polyphenol content, the Folin-Ciocalteu method was used. This method uses the Folin's phenol reagent, which is reduced by phenolic hydroxy group to change color. In measuring the oleuropein content, HPLC analysis was conducted. This is called high-performance liquid chromatography and is a process for separating a certain substance in a system including a stationary phase and a mobile phase.

In measuring the antioxidant potency, ORAC (Oxygen Radical Absorbance Capacity) was determined (reference: Wu, X. et al., J. Agric. Food Chem., m 2004, 52, 4026-4037. The activity exhibited by 1 μmol of Trolox was used as a unit).

In measuring the ultraviolet absorption capacity, a spectrophotometer was used to measure the absorption spectra. The areas of the absorption spectra of ultraviolet regions (UV-A waves: 320 nm-400 nm, UV-B waves: 290 nm-320 nm) were measured and determined as ultraviolet absorption capacity.

[Olive Branch Extract]

(Extraction Solvent)

Olive branch extracts were extracted from dried and ground olive branches using water, 10% of 1,3-butylene glycol (BG), 30% of BG, 50% of BG, 80% of BG, 10% of ethanol (EtOH), 30% of EtOH, 50% of EtOH, and 100% of EtOH as extraction solvents. The cultivar of olive branches used was Mission. The olive branches were added in the amount of 10% by weight with respect to the extraction solvent and subjected to extraction at extraction temperatures of 50° C. to 60° C. for 3 hours. The total polyphenol content (mg/100 g), the oleuropein content (mg/100 g), and the ultraviolet absorption capacity of the resultant olive branch extract were measured and listed in Table 1 and illustrated in FIG. 1.

The result indicates that an olive branch extract having a high total polyphenol content, a high oleuropein content, and a high ultraviolet absorption capacity can be obtained using any of water, 1,3-butylene glycol, and ethanol as an extraction solvent. When 1,3-butylene glycol or ethanol is used as an extraction solvent, the total polyphenol content, the oleuropein content, and the ultraviolet absorption capacity are higher when using 10% to 50% of 1,3-butylene glycol or ethanol.

TABLE 1

| Extraction solvent | Total polyphenol content (mg/100 g) | UV-A waves (320 nm-400 nm) absorption capacity | UV-B waves (290 nm-320 nm) absorption capacity |
| --- | --- | --- | --- |
| Water | 50 | 434 | 350 |
| 10% of BG | 66 | 410 | 368 |
| 30% of BG | 75 | 438 | 397 |
| 50% of BG | 68 | 378 | 375 |
| 80% of BG | 52 | 213 | 245 |
| 10% of EtOH | 70 | 372 | 344 |
| 30% of EtOH | 99 | 625 | 558 |
| 50% of EtOH | 86 | 554 | 531 |
| 100% of EtOH | 27 | 121 | 162 |

(Cultivar of Olive Branch)

Figure 2:
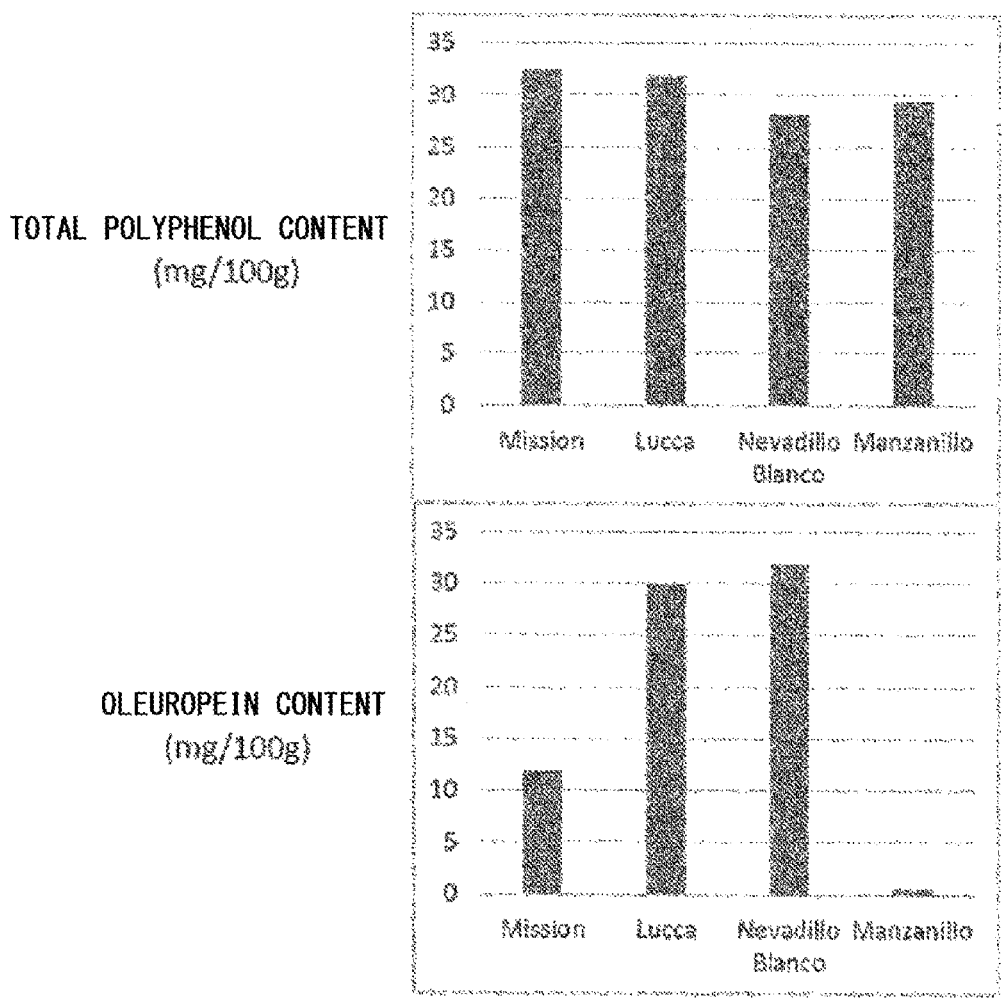
FIG. 2 is a graph illustrating the total polyphenol content (mg/100 g) and the oleuropein content (mg/100 g) of olive branch extracts extracted from a variety of cultivars of olive branches.

Olive branch extracts were extracted from dried and ground olive branches using 30% of 1,3-butylene glycol as an extraction solvent. The cultivars of olive branches used were Mission, Lucca, Nevadillo Banco, and Manzanillo. The olive branches were added in the amount of 10% by weight with respect to the extraction solvent and subjected to extraction at extraction temperatures of 50° C. to 60° C.

for 3 hours. The total polyphenol content (mg/100 g) and the oleuropein content (mg/100 g) of the resultant olive branch extract were measured and illustrated in FIG. 2.

The result indicates that an olive branch extract with a high total polyphenol content can be obtained for any of the cultivars of Mission, Lucca, Nevadillo Blanco, and Manzanillo.

(Extraction Temperature)

Figure 3:
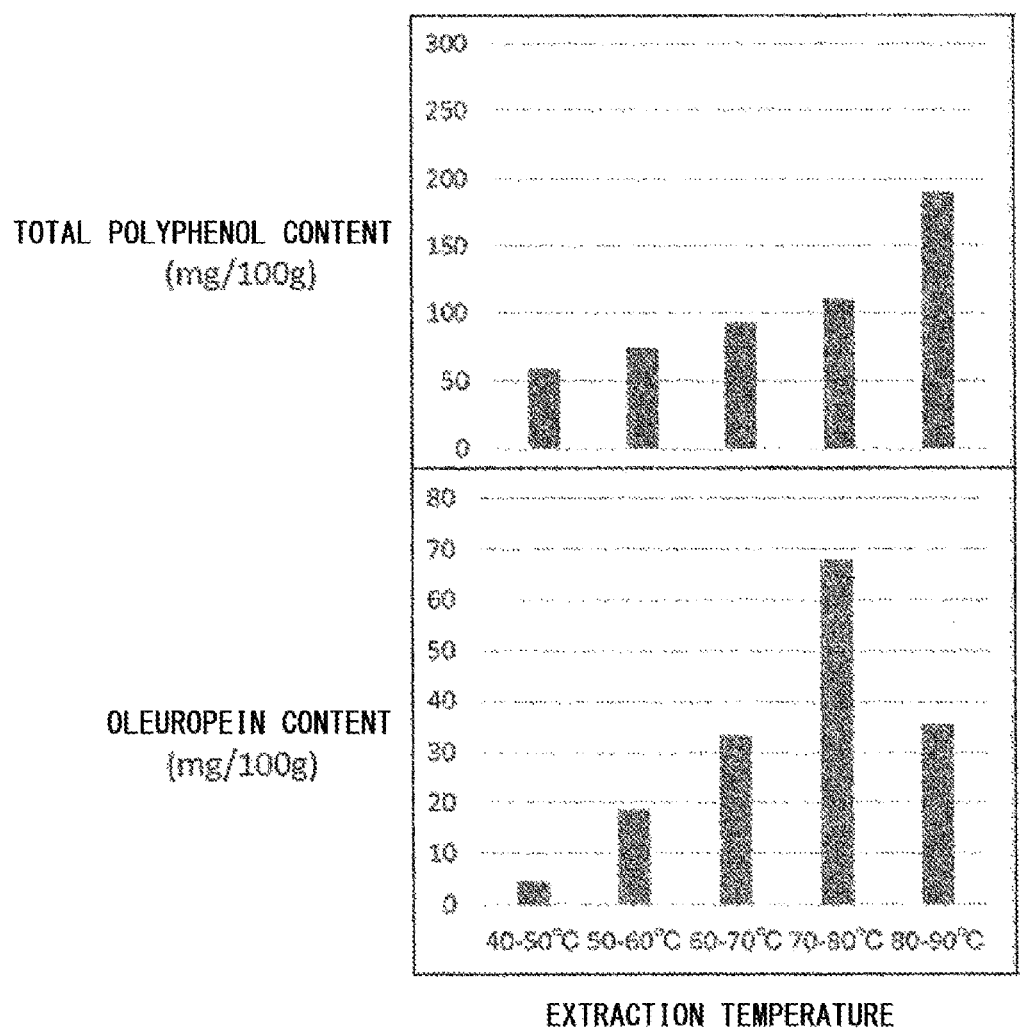
FIG. 3 is a graph illustrating the total polyphenol content (mg/100 g) and the oleuropein content (mg/100 g) of olive branch extracts extracted at a variety of extraction temperatures.

Olive branch extracts were extracted from dried and ground olive branches using 30% of 1,3-butylene glycol as an extraction solvent. The cultivar of olive branches used was Mission. The olive branches were added in the amount of 10% by weight with respect to the extraction solvent and subjected to extraction for 3 hours with the extraction temperature changed stepwise in the range of 30° C. to 100° C. The total polyphenol content (mg/100 g), the total amount of polyphenol per heat quantity (cal) (mg/heat quantity cal), the oleuropein content (mg/100 g), and the ultraviolet absorption capacity of the resultant olive branch extract were measured and listed in Table 2 and illustrated in FIG. 3.

The result indicates that when the extraction temperature is 70° C. or higher, an olive branch extract having a high total polyphenol content, a high oleuropein content, and a high ultraviolet absorption capacity can be extracted. It is also demonstrated that when the extraction temperature is 80° C. or higher, preferably 90° C. or higher, an olive branch extract having a higher total polyphenol content and a higher ultraviolet absorption capacity can be extracted.

TABLE 2

| Extraction temperature | Total polyphenol content (mg/100 g) | Total amount of polyphenol (mg/heat quantity cal) | UV-A waves (320 nm-400 nm) absorption capacity | UV-B waves (290 nm-320 nm) absorption capacity |
| --- | --- | --- | --- | --- |
| 30° C.-40° C. | 60 | 0.015 | 320 | 310 |
| 40° C.-50° C. | 59 | 0.012 | 293 | 277 |
| 50° C.-60° C. | 75 | 0.012 | 438 | 397 |
| 60° C.-70° C. | 93 | 0.013 | 575 | 523 |
| 70° C.-80° C. | 110 | 0.014 | 655 | 594 |
| 80° C.-90° C. | 190 | 0.021 | 969 | 891 |
| 90° C.-100° C. | 296 | 0.030 | 2183 | 1720 |

(Extraction Time)

Figure 4:
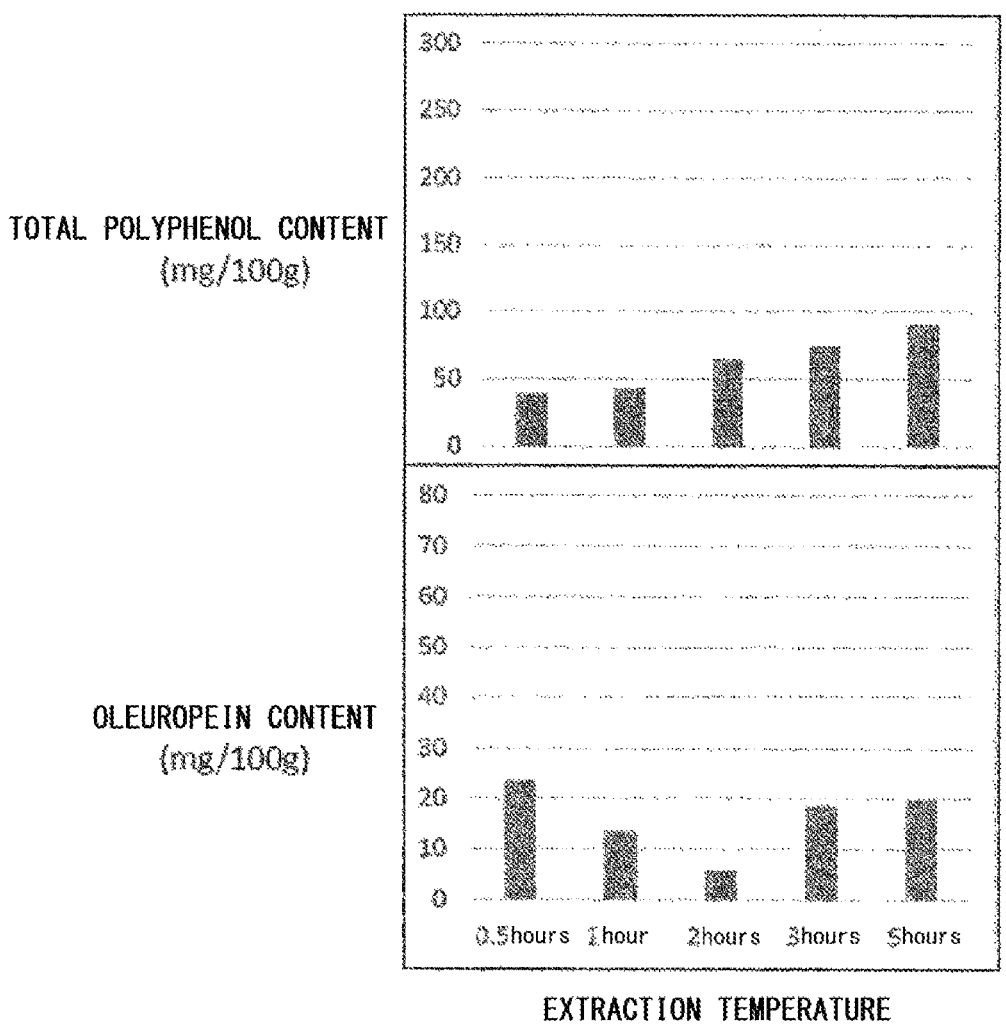
FIG. 4 is a graph illustrating the total polyphenol content (mg/100 g) and the oleuropein content (mg/100 g) of olive branch extracts extracted with a variety of extraction times.

Olive branch extracts were extracted from dried and ground olive branches using 30% of 1,3-butylene glycol as an extraction solvent. The cultivar of olive branches used was Mission. The olive branches were added in the amount of 10% by weight with respect to the extraction solvent and subjected to extraction at extraction temperatures of 50° C. to 60° C. The extraction times were 0.5 hour, 1 hour, 2 hours, 3 hours, and 5 hours. The total polyphenol content (mg/100 g), the total amount of polyphenol per the extraction time (mg/time), the oleuropein content (mg/100 g), and the ultraviolet absorption capacity of the resultant olive branch extract were measured and listed in Table 3 and illustrated in FIG. 4.

The result indicates that the longer the extraction time is, the higher the total polyphenol content and the ultraviolet absorption capacity are, but the lower the total amount of polyphenol per the extraction time is.

TABLE 3

| Extraction time | Total polyphenol content (mg/100 g) | Total amount of polyphenol (mg/time) | UV-A waves (320 nm-400 nm) absorption capacity | UV-B waves (290 nm-320 nm) absorption capacity |
| --- | --- | --- | --- | --- |
| 0.5 hour | 40 | 238 | 141 | 160 |
| 1 hour | 43 | 129 | 208 | 208 |
| 2 hours | 65 | 98 | 361 | 332 |
| 3 hours | 75 | 75 | 438 | 397 |
| 5 hours | 92 | 55 | 498 | 461 |

(Amount of Branches Added)

Figure 5:
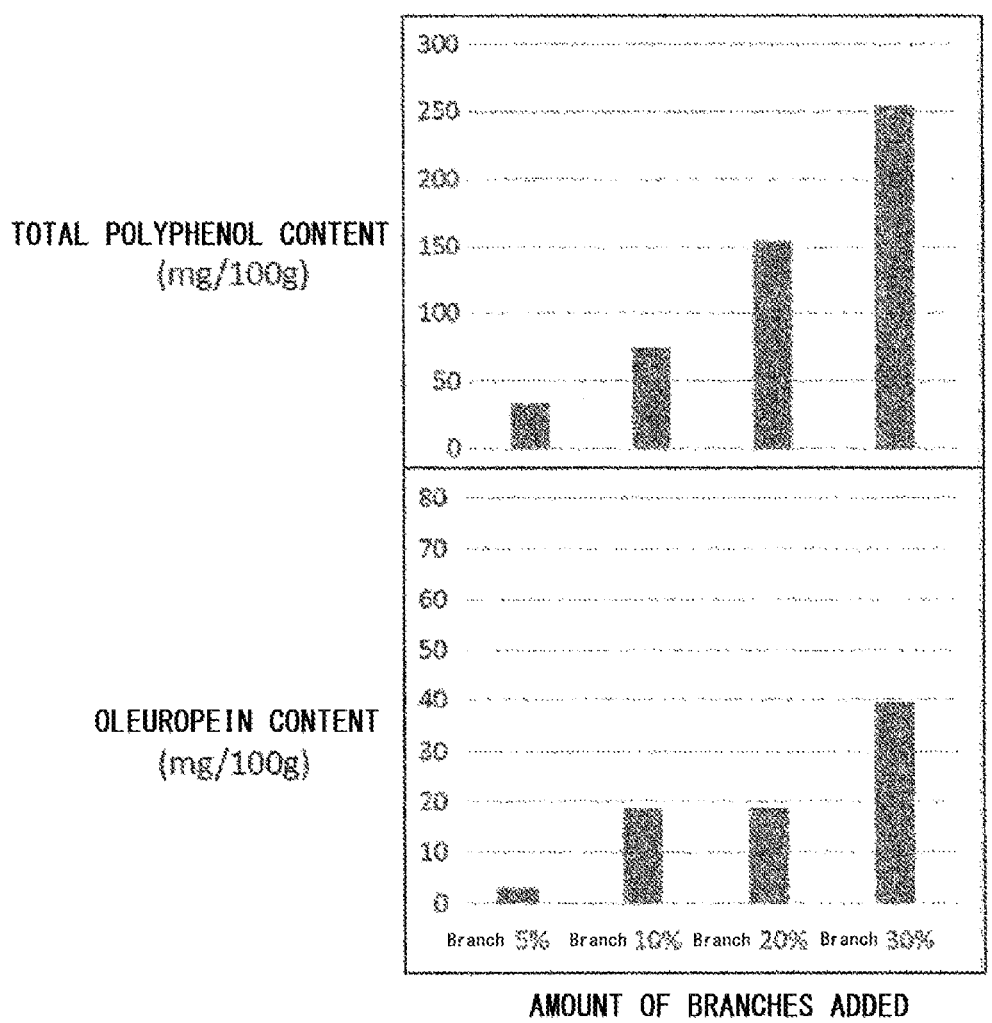
FIG. 5 is a graph illustrating the total polyphenol content (mg/100 g) and the oleuropein content (mg/100 g) of olive branch extracts extracted with a variety of amounts of branch added.

Olive branch extracts were extracted from dried and ground olive branches using 30% of 1,3-butylene glycol as an extraction solvent. The cultivar of olive branches used was Mission. The olive branches were added in the amount of 5%, 10%, 20%, 30%, 40%, or 44% by weight with respect to the extraction solvent and subjected to extraction at extraction temperatures of 50° C. to 60° C. for 3 hours. The total polyphenol content (mg/100 g), the total amount of polyphenol per the amount of branches added (g) (mg/added branches g), the oleuropein content (mg/100 g), and the ultraviolet absorption capacity of the resultant olive branch extract were measured and listed in Table 4 and illustrated in FIG. 5.

The result indicates that when the amount of branches added is not less than 30% by weight, an olive branch extract having a high total polyphenol content, a high oleuropein content, and a high ultraviolet absorption capacity can be extracted.

TABLE 4

| Amount of branches added | Total polyphenol content (mg/100 g) | Total amount of polyphenol (mg/added branches g) | UV-A waves (320 nm-400 nm) absorption capacity | UV-B waves (290 nm-320 nm) absorption capacity |
| --- | --- | --- | --- | --- |
| 5% | 33 | 6.6 | 119 | 142 |
| 10% | 75 | 7.5 | 438 | 397 |
| 20% | 154 | 7.7 | 965 | 802 |
| 30% | 255 | 8.5 | 1692 | 1381 |
| 40% | 330 | 8.3 | 2506 | 2041 |
| 44% | 334 | 7.6 | 2162 | 1836 |

(Comparison of Extraction Conditions)

Olive branch extracts were extracted from dried and ground olive branches using 30% of 1,3-butylene glycol as an extraction solvent under two different extraction conditions. The cultivar of olive branches used was Mission. In Extraction Condition 1 (Comparative Example), the olive branches were added in the amount of 10% by weight with respect to the extraction solvent and subjected to extraction at 50° C. to 60° C. for 3 hours. In Extraction Condition 2 (Example), the olive branches were added in the amount of 30% by weight with respect to the extraction solvent and subjected to extraction at 80° C. to 90° C. for 2 hours. The total polyphenol content (mg/100 g), the oleuropein content (mg/100 g), the ultraviolet absorption capacity, and the antioxidant potency of the resultant olive branch extract were measured and listed in Table 5.

The result indicates that an olive branch extract having a significantly high total polyphenol content, a significantly high oleuropein content, a significantly high ultraviolet absorption capacity, and a significantly high antioxidant potency can be obtained with Extraction Condition 2, compared with Extraction Condition 1.

TABLE 5

| Condition comparison | Total polyphenol content (mg/100 g) | Oleuropein content (mg/100 g) | UV-A waves (320 nm-400 nm) absorption capacity | UV-B waves (290 nm-320 nm) absorption capacity | antioxidant potency ORAC (μmol TE/g) |
|---|---|---|---|---|---|
| Extraction Condition 1 | 75 | 18.6 | 438 | 397 | 14 |
| Extraction Condition 2 | 759 | 122.9 | 3249 | 2535 | 93 |

[Olive Bark Extract]
(Extraction Solvent)

Olive bark extracts were extracted from dried and ground olive bark using water, 30% of 1,3-butylene glycol (BG), and 50% of ethanol (EtOH) as extraction solvents. The cultivar of olive bark used was Mission. The olive bark was added in the amount of 10% by weight with respect to the extraction solvent and subjected to extraction at extraction temperatures of 50° C. to 60° C. for 5 hours. The total polyphenol content (mg/100 g) of the resultant olive bark extract was measured and listed in Table 6.

The result indicates that an olive bark extract having a high total polyphenol content can be extracted using any of water, 1,3-butylene glycol, and ethanol as an extraction solvent.

TABLE 6

| Extraction solvent | Total polyphenol content (mg/100 g) |
|---|---|
| Water | 83 |
| 30% of BG | 143 |
| 50% of EtOH | 162 |

(Amount of Bark Added)

Olive bark extracts were extracted from dried and ground olive bark using 30% of 1,3-butylene glycol (BG) as an extraction solvent. The cultivar of olive bark used was Mission. The olive bark was added in the amount of 5%, 10%, 20%, or 30% by weight with respect to the extraction solvent and subjected to extraction at extraction temperatures of 50° C. to 60° C. for 5 hours. The total polyphenol content (mg/100 g), the total amount of polyphenol per the amount of bark added (g) (mg/added bark g), and the ultraviolet absorption capacity of the resultant olive bark extract were measured and listed in Table 7.

The result indicates that when the amount of bark added is not less than 20% by weight, an olive bark extract having a high total polyphenol content and a high ultraviolet absorption capacity can be extracted.

TABLE 7

| Amount of bark added | Total polyphenol content (mg/100 g) | Total amount of polyphenol (mg/added bark g) | UV-A waves (320 nm-400 nm) absorption capacity | UV-B waves (290 nm-320 nm) absorption capacity |
|---|---|---|---|---|
| 5% | 86 | 17.3 | 712 | 510 |
| 10% | 143 | 14.3 | 1113 | 814 |
| 20% | 272 | 13.6 | 2419 | 1719 |
| 30% | 284 | 9.5 | 2531 | 1876 |

(Extraction Temperature)

Olive bark extracts were extracted from dried and ground olive bark using 30% of 1,3-butylene glycol as an extraction solvent. The cultivar of olive bark used was Mission. The olive bark was added in the amount of 10% by weight with respect to the extraction solvent and subjected to extraction for 5 hours with extraction temperature changed stepwise in the range of 40° C. to 90° C. The total polyphenol content (mg/100 g), the total amount of polyphenol per heat quantity (cal) (mg/heat quantity cal), and the ultraviolet absorption capacity of the resultant olive bark extract were measured and listed in Table 8.

The result indicates that when the extraction temperature is 70° C. or higher, an olive bark extract having high total polyphenol content and ultraviolet absorption capacity can be extracted.

TABLE 8

| Extraction temperature | Total polyphenol content (mg/100 g) | Total amount of polyphenol (mg/heat quantity cal) | UV-A waves (320 nm-400 nm) absorption capacity | UV-B waves (290 nm-320 nm) absorption capacity |
|---|---|---|---|---|
| 40° C.-50° C. | 106 | 0.021 | 896 | 663 |
| 50° C.-60° C. | 143 | 0.024 | 1113 | 814 |
| 60° C.-70° C. | 178 | 0.025 | 1387 | 1062 |
| 70° C.-80° C. | 315 | 0.039 | 1733 | 1243 |
| 80° C.-90° C. | 275 | 0.031 | 1750 | 1275 |

(Extraction Time)

Olive bark extracts were extracted from dried and ground olive bark using 30% of 1,3-butylene glycol as an extraction solvent. The cultivar of olive bark used was Mission. The olive bark was added in the amount of 10% by weight with respect to the extraction solvent and subjected to extraction at extraction temperatures of 50° C. to 60° C. The extraction times were 0.5 hour, 1 hour, 2 hours, 3 hours, and 5 hours. The total polyphenol content (mg/100 g), the total amount of polyphenol per the extraction time (mg/time), and the ultraviolet absorption capacity of the resultant olive bark extract were measured and listed in Table 9.

The result indicates that the longer the extraction time is, the higher the total polyphenol content and the ultraviolet absorption capacity are, but the lower the total amount of polyphenol per the extraction time is.

TABLE 9

| Extraction time | Total polyphenol content (mg/100 g) | Total amount of polyphenol (mg/time) | UV-A waves (320 nm-400 nm) absorption capacity | UV-B waves (290 nm-320 nm) absorption capacity |
| --- | --- | --- | --- | --- |
| 0.5 hour | 66 | 397 | 830 | 600 |
| 1 hour | 84 | 252 | 993 | 714 |
| 2 hours | 120 | 180 | 1142 | 818 |
| 3 hours | 134 | 134 | 1044 | 763 |
| 5 hours | 143 | 86 | 1113 | 814 |

(Comparison of Extraction Solvents Under Optimum Conditions)

Olive bark extracts were extracted from olive bark using a variety of extraction solvents under the optimum conditions derived from the results above. Water, 30% of 1,3-butylene glycol, and 50% of ethanol were used as extraction solvents. The extraction temperatures were 70° C. to 80° C., the extraction time was 5 hours, and the amount of bark added was 20% by weight with respect to the extraction solvent. The total polyphenol content (mg/100 g) and the ultraviolet absorption capacity of the resultant olive bark extract were measured and listed in Table 10.

The result indicates that when 30% of 1,3-butylene glycol is used as an extraction solvent, the total polyphenol content and the ultraviolet absorption capacity are highest.

TABLE 10

| Extraction condition | Total polyphenol content (mg/100 g) | UV-A waves (320 nm-400 nm) absorption capacity | UV-B waves (290 nm-320 nm) absorption capacity |
| --- | --- | --- | --- |
| Water | 151 | 2436 | 1851 |
| 30% of BG | 479 | 3766 | 2652 |
| 50% of EtOH | 336 | 2672 | 1855 |

(Comparison of Extraction Conditions)

Olive bark extracts were extracted from dried and ground olive bark using 30% of 1,3-butylene glycol as an extraction solvent under two different extraction conditions. The cultivar of olive bark used was Mission. In Extraction Condition 3 (Comparative Example), the olive bark was added in the amount of 10% by weight with respect to the extraction solvent and subjected to extraction at 50° C. to 60° C. for 5 hours. In Extraction Condition 4 (Example), the olive bark was added in the amount of 20% by weight with respect to the extraction solvent and subjected to extraction at 70° C. to 80° C. for 5 hours. The antioxidant potency of the resultant olive bark extract was measured and listed in Table 11.

The result indicates that an olive bark extract having a significantly high antioxidant potency can be obtained with Extraction Condition 4, compared with Extraction Condition 3.

TABLE 11

| Antioxidant potency | Antioxidant potency ORAC (µmol TE/g) |
| --- | --- |
| Extraction Condition 3 | 11 |
| Extraction Condition 4 | 33 |

Although the embodiment according to the present invention has been described above, it is needless to say that the present invention is not limited thereto and is susceptible of various modifications and changes without departing from the spirit of the invention.

INDUSTRIAL APPLICABILITY

The ultraviolet blocking agent according to the present invention can be suitably used in pharmaceutical drugs, medicines, cosmetics, and foods having an ultraviolet blocking action.

The invention claimed is:

1. A method for producing an olive branch extract having a high oleuropein content comprising:
   crushing at least a portion of dried olive branch; and
   extracting olive branch extract from the crushed olive branch with an extraction solvent,
      wherein the olive variety is at least one selected from the group consisting of Lucca, Mission, and Nevadillo Blanco,
      the added branch amount of olive branch to the extraction solvent is 10% by weight or more,
      the extraction solvent is 30% to 50% 1,3-butylene glycol, and
      the extraction is performed at a temperature in a range of 70° C. to 80° C.

2. The method according to claim 1, wherein the added branch amount of olive branch to the extraction solvent is 20% by weight or more.

3. The method according to claim 1, wherein the extraction solvent is 50% 1,3-butylene glycol.

4. The method according to claim 1, wherein the olive variety is at least one selected from the group consisting of Lucca and Nevadillo Blanco.

5. The method according to claim 1, wherein the portion of dried olive branch is olive bark.

6. The method according to claim 2, wherein the portion of dried olive branch is olive bark.

7. The method according to claim 3, wherein the portion of dried olive branch is olive bark.

8. The method according to claim 4, wherein the portion of dried olive branch is olive bark.

* * * * *